United States Patent
Vasudeva (10) Patent No.: US 10,470,920 B1
(45) Date of Patent: Nov. 12, 2019

(54) BACKFLOW PREVENTING MENSTRUAL CUP

(71) Applicant: Karina Vasudeva, Chevy Chase, MD (US)

(72) Inventor: Karina Vasudeva, Chevy Chase, MD (US)

( * ) Notice: Subject to any disclaimer, the term of this patent is extended or adjusted under 35 U.S.C. 154(b) by 0 days.

(21) Appl. No.: 16/563,904

(22) Filed: Sep. 8, 2019

(51) Int. Cl.
*A61F 5/455* (2006.01)
*A61F 13/20* (2006.01)

(52) U.S. Cl.
CPC ............ *A61F 5/4553* (2013.01); *A61F 5/455* (2013.01); *A61F 13/2045* (2013.01)

(58) Field of Classification Search
CPC .... A61F 5/4553; A61F 5/455; A61F 13/2045; A61F 6/06; A61F 6/08
See application file for complete search history.

(56) References Cited

U.S. PATENT DOCUMENTS

| 5,342,331 | A | * | 8/1994 | Silber | ............... | A61F 5/4553 604/330 |
|---|---|---|---|---|---|---|
| 2013/0110060 | A1 | * | 5/2013 | Shihata | ............... | A61F 5/4553 604/330 |
| 2017/0189222 | A1 | * | 7/2017 | Lin | ............... | A61F 5/4553 |

FOREIGN PATENT DOCUMENTS

KR 101901532 B1 * 9/2018
WO WO-2018186533 A1 * 10/2018 ........... A61F 5/4553

OTHER PUBLICATIONS

Intimina Lily Cup Compact, target.com (Year: 2019).*
Translation of WO 2018/186533 (Year: 2019).*
Translation of KR 101901532 (Year: 2019).*
Levine, "Menstrual cup linked to toxic shock syndrome, new study finds," Consumer Reports, Apr. 20, 2018. Retrieved from URL www.consumerreports.org on Sep. 1, 2019.
Mitchell et al., "A confirmed case of toxic shock syndrome associated with the use of a menstrual cup," Canadian Journal of Infectious Diseases & Medical Microbiology, vol. 26, No. 4, Jul.-Aug. 2015, pp. 218-220.
Nonfoux et al., "Impact of currently marketed tampons and menstrual cups on *Staphylococcus aureus* growth and toxic shock syndrome toxin 1 production in vitro," Applied and Environmental Microbiology, vol. 84, issue 12, Jun. 2018, pp. 1-12. Retrieved from URL http://aem.asm.org on Jul. 29, 2019.

* cited by examiner

*Primary Examiner* — Adam Marcetich
*Assistant Examiner* — Jessica A Arble (57) ABSTRACT

A backflow and leakage preventing menstrual cup for collecting menstrual discharge is disclosed. The menstrual cup has a safety feature that prevents backflow of menstrual blood back into vagina and uterus, which minimizes contact with the collected menstrual blood and prevents the risk of infection and toxic shock syndrome (TSS) to the user. This safety feature also stops accidental leakage during use and prevents spillage of menstrual blood when the cup is removed by user. The cup is designed to be easily and quickly emptied.

18 Claims, 5 Drawing Sheets

BACKFLOW PREVENTING MENSTRUAL CUP

BACKGROUND OF THE INVENTION

Field of the Invention

The present invention discloses a backflow preventing menstrual cup, and belongs to the technical field of menstrual hygiene, and more particularly to intravaginal menstrual devices for collecting menstrual fluids. In particular, the present invention discloses a flexible menstrual cup that is designed to prevent leakage during use or backflow of menstrual fluid back into the vaginal canal, thereby protecting its users from serious infections.

Description of the Prior Art

In recent times, use of tampons and menstrual cups has become very popular due to desire for convenience and greater environmental awareness. However, there are many serious deficiencies and disadvantages inherent in the commercially available tampons and menstrual cups, which can pose serious health and safety risks to the users.

There have been many well-documented reports of women contracting infections and suffering menstrual toxic shock syndrome as a result of using tampons or menstrual cups. Menstrual toxic shock syndrome (TSS) is a dangerous and potentially deadly condition caused by a type of bacteria that produce debilitating toxins. It is well known that healthy women who use intravaginal menstrual protection products such as tampons, and in many cases even menstrual cups, become vulnerable to vaginal colonization by bacteria such as *Staphylococcus aureus* (*S. aureus*), which in some cases is capable of producing a toxin called Toxic Shock Syndrome Toxin 1 (TSST-1). The toxin TSST-1 can trigger severe inflammatory response in the human body, which can result in sudden high fever, nausea, vomiting, diarrhea, abnormally low blood pressure or hypotension, skin rashes and, in the some severe cases, organ failure.

The use of tampons and menstrual cups can cause prolonged contact with menstrual blood while such devices are in use. In particular, when women using a menstrual cup are in a reclined position, the menstrual blood collected in the cup can spill out of the cup and flow back into the vagina and/or uterus, thereby rendering users susceptible to dangerous infections.

Additionally, the commercially available menstrual cups do not provide adequate protection against accidental leakage of menstrual blood while in use, and such cups are not designed to prevent spillage of collected blood when the cup is removed from the vagina. In view of all the design flaws and disadvantages described above, menstrual cups have failed to achieve widespread acceptance from women.

Therefore, there is an urgent need for a safe and easy to use menstrual hygiene device that eliminates or minimizes the risk of vaginal infection, and importantly, protects users from potentially deadly infection such as TSS due to prolonged exposure to the menstrual blood.

There is also an urgent need for a menstrual hygiene device that would prevent accidental leakage of menstrual blood while in use and prevent spillage of collected blood during the process if removal from the vagina.

Additionally, there is also a need for a reusable and durable menstrual hygiene device that can be used for several years without replacement, is easy to clean and has negligible harmful impact on the environment.

Therefore, it is an object of the present invention to address and alleviate the above highlighted deficiencies associated with the commercially available menstrual hygiene devices. In particular, it is an object of the present invention to provide a safe and easy to use menstrual hygiene device that minimizes contact with the collected menstrual blood and thereby reduces the risk of vaginal infection. It is further an object of the present invention to offer a device capable of stopping accidental leakage of menstrual blood while in use and preventing spillage of collected blood when it is removed from the vagina. It is an additional object of the present invention to propose a reusable and durable menstrual hygiene device that can be used for several years without replacement, is easy to clean and does not harm the environment.

BRIEF SUMMARY OF THE INVENTION

The invention disclosed herein is an intravaginal menstrual cup for collecting menstrual discharge. The cup is made from a flexible, non-absorbent material and has a shape that can be selectively changed between an elongated configuration and a compact configuration. The menstrual cup comprises a storage receptacle, a barrier funnel, and a discharge duct, wherein an internal surface of the storage receptacle defines a cavity for collecting and storing menstrual blood.

The barrier funnel provides the cup with a novel safety feature that directs menstrual blood into the storage receptacle and prevents its backflow or discharge until the user is ready to empty the cup. The barrier funnel is made from a flexible material and connected to the storage receptacle by a first flexible hinge that allows the barrier funnel to be moved between a folded position and an open position. The barrier funnel is further connected to the discharge duct by a second flexible hinge, which allows the discharge duct to move between a retracted position and an extended position.

The cup is placed in the vaginal canal in its compact configuration in which the barrier funnel and the discharge duct are disposed in their respective folded and retracted positions inside the cup cavity. With the barrier funnel being in the folded position, an upper external surface of the barrier funnel guides menstrual discharge toward its center and allows it to flow unhindered into the cavity of the storage receptacle. A lower internal surface of the barrier funnel helps confine the menstrual blood within the storage receptacle even when the menstrual cup is inverted or disposed in an inclined orientation, thereby preventing the menstrual blood collected in the storage receptacle from flowing back into the vagina in a simple yet effective manner.

A handle is attached to the bottom of the storage receptacle, which allows users to remove the cup from the vaginal canal. When the menstrual cup is removed, it is emptied by first pulling the barrier funnel and discharge duct outwardly so as to expand the cup into its elongated configuration, and then inverting the cup to allow the menstrual blood to drain under gravity.

The novel safety feature described above prevents backflow of menstrual blood from the cup cavity back into the vagina and/or uterus, which minimizes contact with the menstrual fluid collected in the cup and thereby prevents the risk of infection and toxic shock syndrome (TSS) to the user. This safety feature also stops accidental leakage during use and prevents spillage of menstrual fluid when the cup is removed from the vaginal canal by the user. The menstrual cup is also designed to be easily and quickly emptied.

These as well as other advantages of the present invention will be more apparent from the following detailed description and drawings. It is understood that changes in the specific structure shown and described may be made within the scope of the claims, without departing from the spirit of the invention.

BRIEF DESCRIPTION OF THE DRAWINGS

The novel features of this invention can be best understood from the accompanying drawings, in which similar reference characters refer to similar parts. A more complete understanding of the invention and its advantages will be apparent from a review of the detailed description in conjunction with the following drawings, in which.

DETAILED DESCRIPTION OF THE INVENTION

Figures 1, 2:
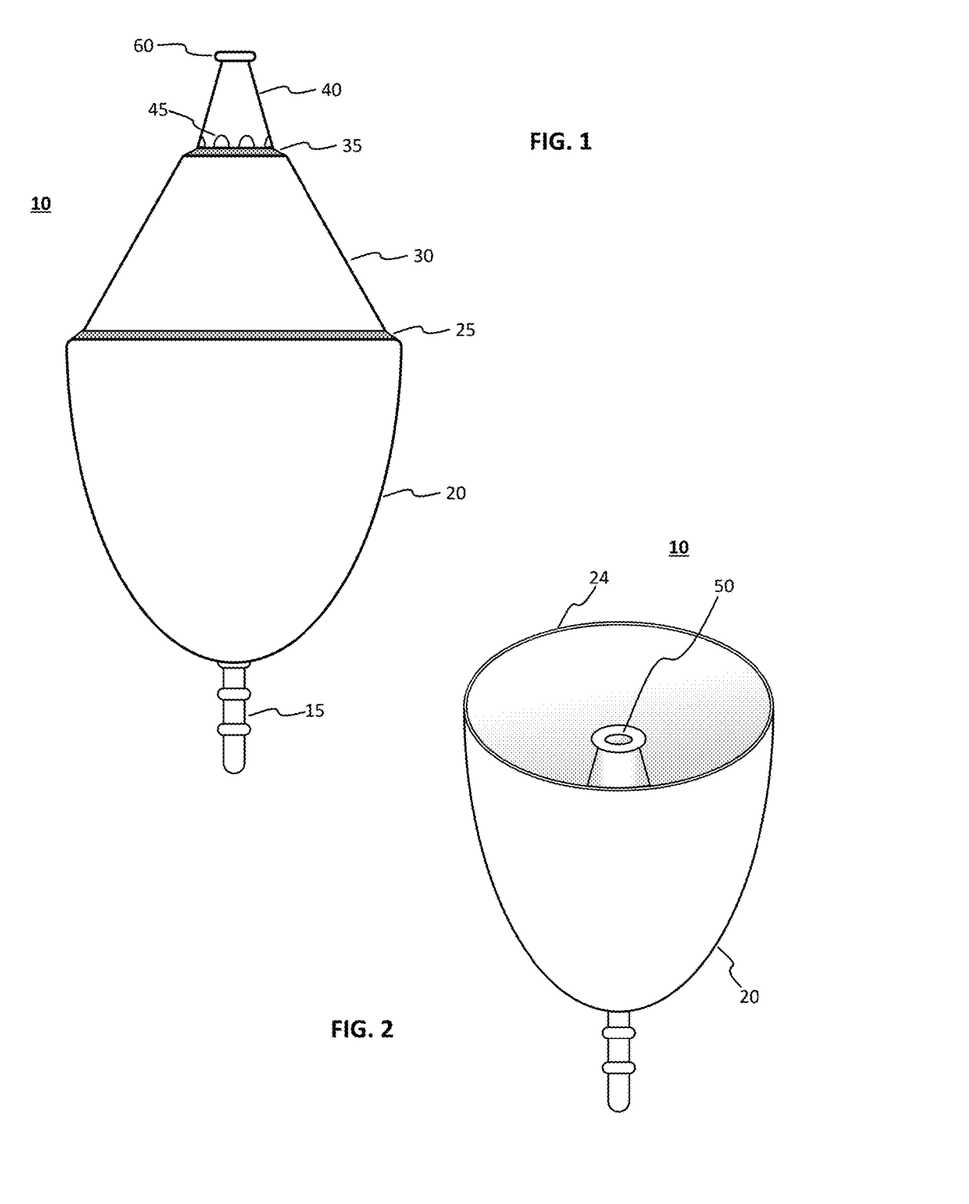
FIG. 1 illustrates an elevation view of the menstrual cup in an elongated configuration.
FIG. 2 illustrates a perspective view of the menstrual cup in a compact configuration.
Figures 5, 6:
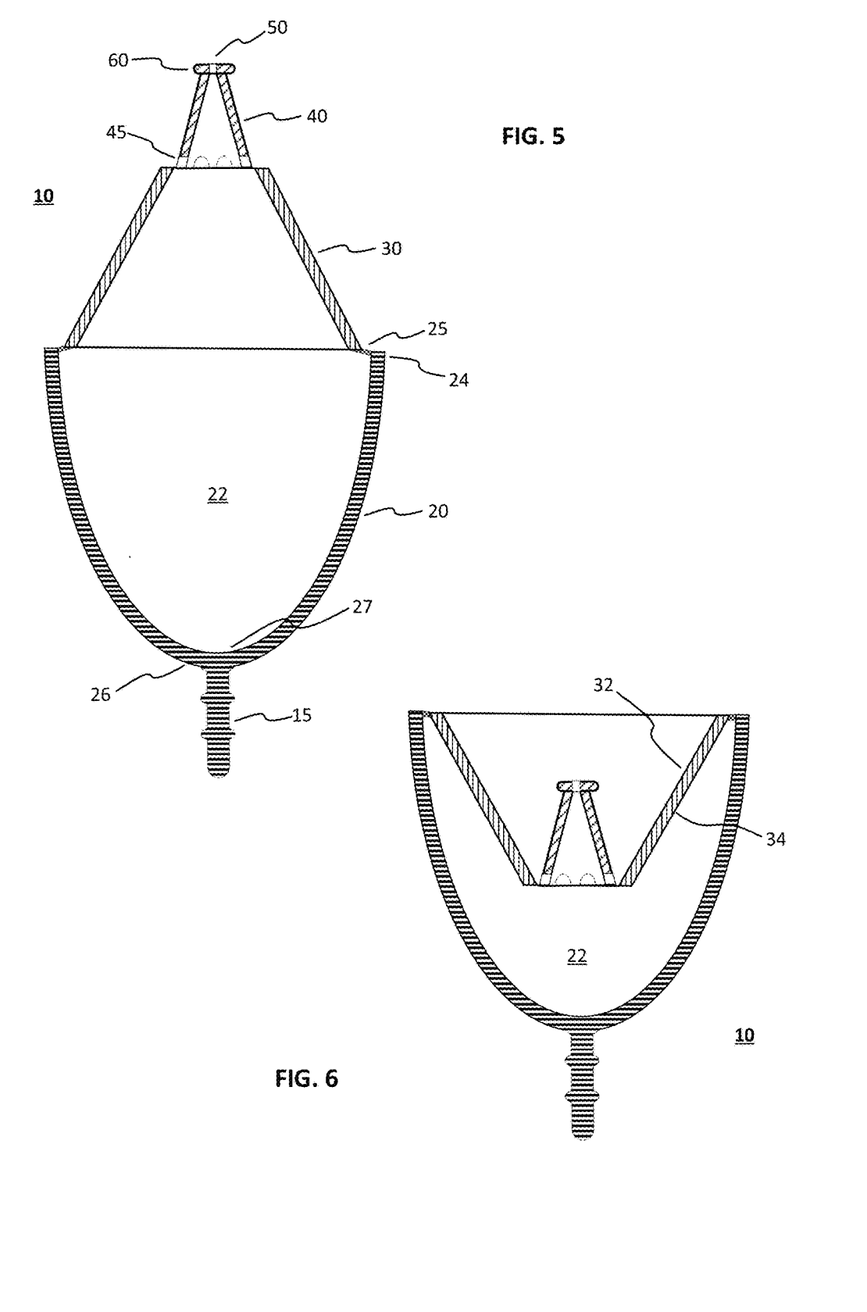
FIG. 5 illustrates a cross-sectional view of the menstrual cup in the elongated configuration taken along line A-A in FIG. 3.
FIG. 6 illustrates a cross-sectional view of the menstrual cup in the compact configuration taken along line B-B in FIG. 4.

FIG. 1 shows a flexible menstrual cup 10 that is made from a flexible, non-absorbent material and has a shape that can be selectively changed between an elongated configuration and a compact configuration. The menstrual cup comprises three adjacent portions: a storage receptacle 20, a barrier funnel 30, and a discharge duct 40, each having a wall with internal and external surfaces. FIG. 5 shows the internal surface of the storage receptacle that defines a cavity 22 for collecting and storing menstrual blood when the cup is disposed in the vagina.

The menstrual cup 10 further comprises a first flexible hinge 25 that connects an upper rim 24 of the storage receptacle 20 to the barrier funnel 30, which enables the barrier funnel 30 to move relative to the storage receptacle 20. The menstrual cup 10 also comprises a second flexible hinge 35 that connects the barrier funnel 30 to the discharge duct 40, which enables the discharge duct 40 to move relative to the barrier funnel 30. Flexible hinge is also known in the art as living hinge or film hinge, and such alternative terminology may be used interchangeably to imply the same structure.

Referring to FIG. 1 and FIG. 6, when the menstrual cup 10 is in one of the elongated and compact configurations, the first flexible hinge 25 and the second flexible hinge 35 are spaced apart from each other along a central longitudinal axis of the menstrual cup 10. The first flexible hinge 25 and the second flexible hinge 35 are disposed in substantially parallel planes, but they may optionally be disposed in non-parallel planes. Further, the first flexible hinge 35 and the second flexible hinge 35 are preferably substantially coaxial, but they can optionally be non-coaxial.

Referring to FIG. 5 and FIG. 6, the second flexible hinge 35 has a diameter that is less than a diameter of the first flexible hinge 25. The ratio of the diameter of the second flexible hinge 35 to the diameter of the first hinge 25 is less than 0.50, and preferably about 0.25. However, such diameter ratio can alternatively be selected in any range of 0.10-0.30, 0.30-0.50, 0.50-0.70 or 0.70-0.90.

Figures 3, 4:
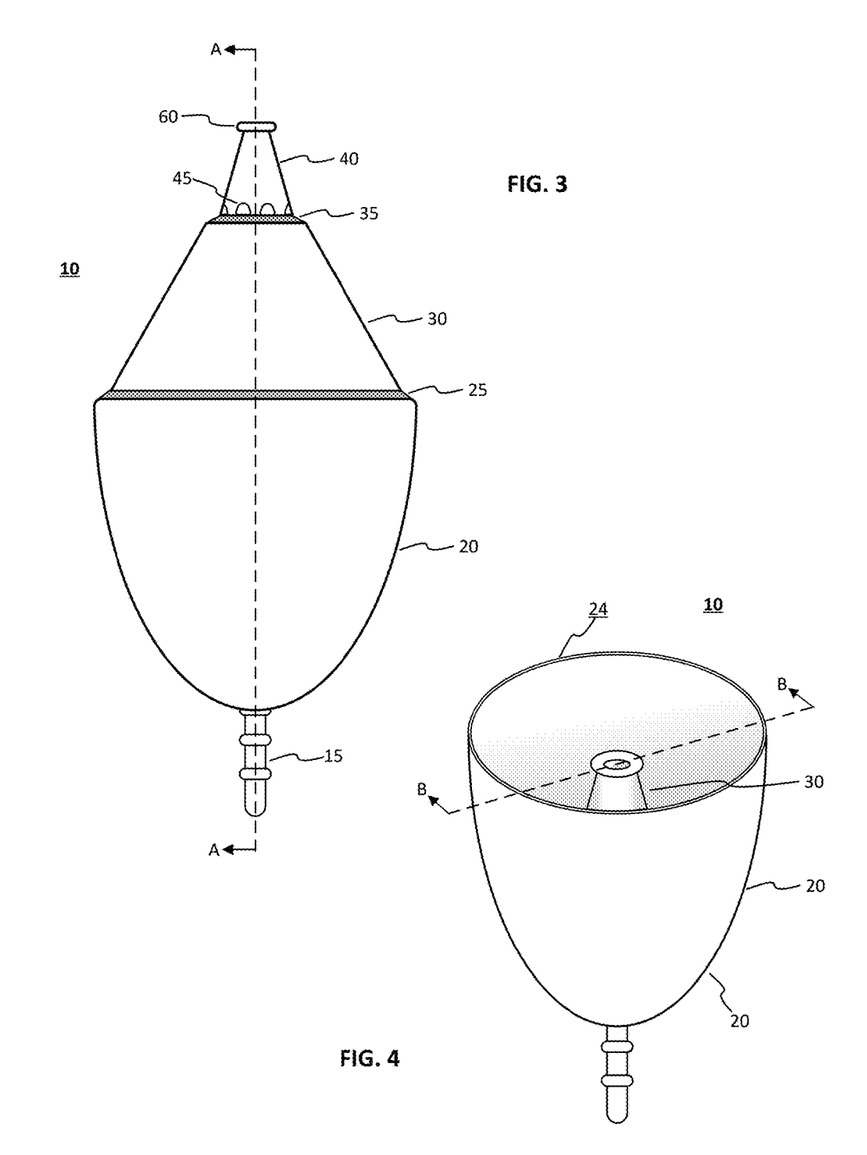
FIG. 3 illustrates an elevation view similar to FIG. 1, identifying additional parts of the menstrual cup in the elongated configuration.
FIG. 4 illustrates a perspective view similar to FIG. 2, identifying additional parts of the menstrual cup in the compact configuration.

FIG. 3 shows the flexible menstrual cup 10 in an elongated configuration in which the barrier funnel 30 and the discharge duct 40 extend or protrude substantially outside the storage receptacle 20. When in the elongated configuration, the second flexible hinge 35 is also disposed outside the storage receptacle 20. In the elongated configuration, the menstrual cup 10 is configured for emptying, cleaning, disinfection, and/or storage after use. The internal structure of the menstrual cup in the elongated configuration is visible in the cross-sectional view shown in FIG. 5.

FIG. 4 shows the flexible menstrual cup 10 in a compact configuration in which the barrier funnel 30 and the discharge duct 40 are retracted or withdrawn substantially inside the storage receptacle 20. When in the compact configuration, the second flexible hinge 35 is also disposed inside the storage receptacle 20. The menstrual cup 10 is placed inside the vagina in the compact configuration for collection and storage of menstrual discharge. The internal structure of the menstrual cup in the compact configuration is visible in the cross-sectional view shown in FIG. 6.

The storage receptacle 20 has a rounded outer profile and can be shaped substantially as a semi-ellipsoid, semi-ovoid, semi-spherical or hemispherical, or a related shape. It has a closed bottom 26 with a generally curved outer profile. The storage receptacle 20 also has a retrieving handle 15 extending downwardly from the closed bottom 26. The retrieving handle 15 is shaped as an elongated stem and configured to be gripped by a user's fingers, or with an implement, to pull the menstrual cup 10 out of the vaginal canal. The retrieving handle 15 can be made as a flexible, semi-rigid, or substantially rigid structure. Instead of being shaped as an elongated stem, the retrieving handle 15 can alternatively be formed as a ring attached to the closed bottom 26. The ring-shaped handle would allow a user to insert a finger in the ring and pull the menstrual cup 10 out of the vaginal canal.

The barrier funnel 30 is made from a flexible material and connected to the storage receptacle 20 by the first hinge 25, which allows the barrier funnel 30 to be moved substantially along the longitudinal axis of the menstrual cup 10 between a folded position and an open position. FIG. 5 and FIG. 6 illustrate how the first flexible hinge 25 enables the barrier funnel 30 to be moved relative to the storage receptacle 20. As seen in these figures, the barrier funnel 30 is movable about the first flexible hinge 25 between the folded position and the open position. When in the open position shown in FIG. 3 and FIG. 5, the barrier funnel 30 is disposed substantially outside the storage receptacle 20, and the internal surface 34 of the barrier funnel 30 forms an obtuse angle with respect to the adjacent internal surface of the storage receptacle 20. When in the folded position shown in FIG. 4 and FIG. 6, the barrier funnel 30 is disposed substantially inside the storage receptacle 20, and the internal surface 34 of the barrier funnel 30 forms an acute angle with respect to the adjacent internal surface of the storage receptacle 20.

The barrier funnel 30 may optionally comprise one or more intermediate flexible hinges (not shown) disposed between the first flexible hinge 25 and the second flexible hinge 35. The intermediate hinge or hinges allow the barrier funnel 30 to move easily between the folded and extended positions.

Additionally, one or more pressure-relief notches or holes (not shown) may optionally be provided on or proximate the receptacle rim 24, which can be evenly spaced about the receptacle rim 24. The pressure-relief notches or holes can facilitate removal of the menstrual cup from the vagina by precluding the formation of a vacuum within the vagina during the removal process.

The discharge duct 40 is made from a flexible material and connected to the barrier funnel 30 by the second flexible hinge 35, which allows the discharge duct 40 to be moved substantially along the longitudinal axis of the menstrual cup 10 between a retracted position and an extended position. FIG. 5 and FIG. 6 illustrate how the second flexible hinge 35 allows the discharge duct 40 to be moved relative to the barrier funnel 30 and the storage receptacle 20. As seen in these figures, the discharge duct 40 is movable about the second flexible hinge 35 between the retracted position and the extended position. When in the extended position seen in FIG. 3 and FIG. 5, the discharge duct 40 and the second flexible hinge 35 are disposed substantially outside the storage receptacle 20, and the external surface of the discharge duct 40 forms an obtuse angle with respect to the adjacent external surface 32 of the barrier funnel 30. When in the retracted position seen in FIG. 4 and FIG. 6, the discharge duct 40 and the second flexible hinge 35 are disposed substantially inside the storage receptacle 20, and the external surface of the discharge duct 40 forms an acute angle with respect to the adjacent external surface 32 of the barrier funnel 30.

Figure 7:
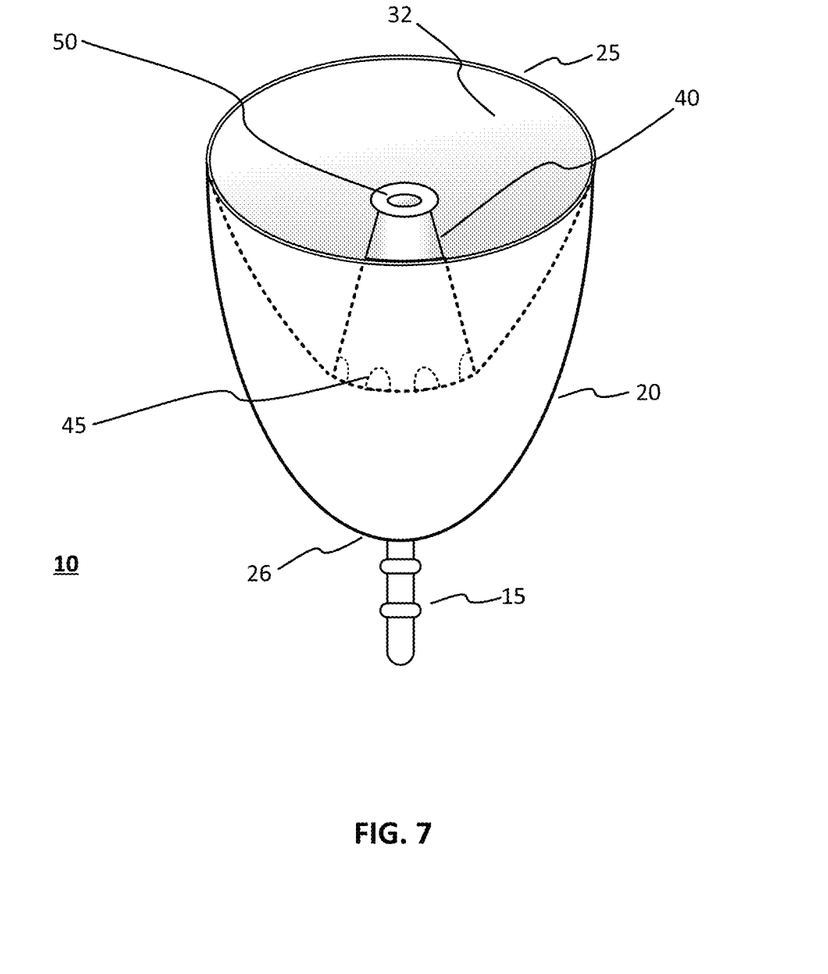
FIG. 7 illustrates a perspective view of the menstrual cup in the compact configuration, showing a retracted portion of the barrier funnel in phantom lines.

Referring to FIG. 1 and FIG. 7, one or more inlet apertures 45 are provided at or substantially close to a lower end, or base, of the discharge duct 40. The inlet apertures 45 are located substantially proximate the second flexible hinge 35. When the menstrual cup is disposed in a collection mode inside the vaginal canal, the inlet apertures 45 allow passage of menstrual discharge into the cavity 22 of the storage receptacle 20. The inlet apertures 45 can be evenly distributed around the base of the discharge duct 40. As shown in FIG. 1, the inlet apertures 45 are shaped as semi-ellipse, but they can optionally be given any other geometric shape, such as semi-circle, circle, ellipse, square, rectangle, triangle, narrow slit resembling a marquise, etc. The inlet apertures 45 may optionally be extended into, or formed exclusively on, the second flexible hinge 35 and/or the barrier funnel 30. The inlet apertures 45 are sized to allow unhindered passage of the menstrual discharge—which includes menstrual blood, blood clots, and discarded biological material such as endometrial tissue shed during menstruation—into the cavity 22 of the storage receptacle 20.

At least one discharge aperture 50 is provided at or substantially proximate an upper end of the discharge duct 40. The upper end of the discharge duct 40 is shaped like a knob 60, which allows a user to grab and extend the discharge duct 40 into the extended position shown in FIG. 1 and FIG. 5 for emptying the menstrual cup 10. The discharge aperture 50 is preferably located centrally in the knob 60, but it can alternatively be formed just below the knob 60.

When the menstrual cup 10 is positioned inside the vagina in the compact configuration, the barrier funnel 30 provides the menstrual cup 10 with a safety feature that directs menstrual blood into the storage receptacle 20 and creates a barrier to prevent backflow or draining of the blood until the user is ready to empty the cup. With the barrier funnel 30 being in the folded position, the external surface 32 of the barrier funnel 30 guides menstrual discharge downwardly toward its center and allows it to flow unhindered through the inlet apertures 45 into the cavity 22. The internal surface 34 of the barrier funnel helps confine the menstrual blood within the storage receptacle 20 even when the menstrual cup is inverted or disposed in an inclined orientation, thereby preventing the menstrual blood collected in the storage receptacle from flowing back into the vagina or the uterus.

Figure 8:
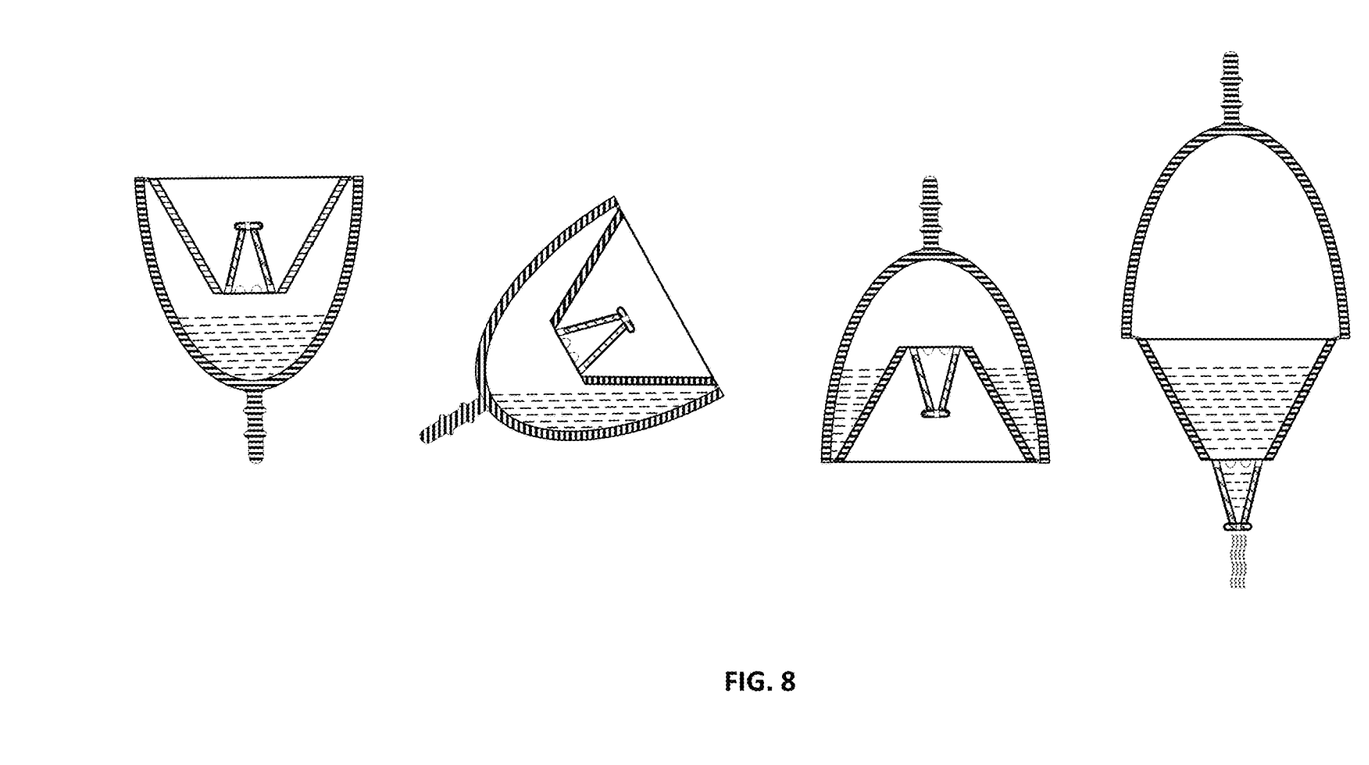
FIG. 8 is a schematic representation of the menstrual cup in sequential cross-sectional views to show collection, retention and draining of the menstrual discharge in different orientations of the cup.

When the menstrual cup 10 is removed from the vagina, it is emptied by first pulling the knob 60 to position the barrier funnel 30 and the discharge duct 40 into their respective open and extended positions. Once the cup 10 is expand to its elongated configuration, it is then inverted partially or completely as illustrated in FIG. 8. This allows the collected menstrual blood to flow out of the storage receptacle 20 under gravity and get discharged through the discharge aperture 50. FIG. 6 illustrates a schematic representation of the menstrual cup in sequential cross-sectional views to show collection, retention and draining of the menstrual discharge in different orientations of the cup.

In the preferred form, the wall of the barrier funnel 30 can be as thick or substantially thinner than the wall of the storage receptacle 20. Additionally, the wall of the barrier funnel 30 can be as flexible or substantially more flexible than the wall of the storage receptacle 20. Making the wall of the barrier funnel 30 thinner and more flexible can facilitate folding and opening of the barrier funnel 30 about the first hinge 25.

Additionally, the wall of the discharge duct 40 can be as thick or substantially thicker than the wall of the barrier funnel 30. Further, the wall of the discharge duct 40 can be as flexible or substantially more rigid than the wall of the barrier funnel 30. Making the wall of the discharge duct 40 thicker and more rigid makes it easier to transfer a pushing or pulling force for folding or opening the barrier funnel 30 about the first hinge 25.

Referring to FIG. 5 and FIG. 6, the receptacle rim 24 and a bottom 27 of the cavity 22 are separated by a vertical distance that defines a depth of the cavity 22. When the menstrual cup 10 is in compact configuration with the barrier funnel 30 folded inwardly, the second flexible hinge 35 and a distal edge 38 of the barrier funnel are disposed approximately midway inside the cavity at substantially 50% of the cavity depth. However, the second flexible hinge 35 and the distal edge 38 of the barrier funnel can alternatively be disposed at a different depth inside the cavity, as measured from the receptacle rim 24, without departing from the scope of the invention. For example, it is possible to optionally position the second flexible hinge 35 and the distal edge 38 of the barrier funnel 30 within a depth range that is substantially 10-25%, 25-50%, 50-75%, 75-90% or greater than 90% of the depth of the cavity 22, as measured from the rim 24.

The menstrual cup 10 of the present invention can be fabricated by procedures well known in the industry, such as by a molding process, and can be formed as a single-piece or multiple-piece device. The menstrual cup is made from a flexible, elastic and non-absorbent material, preferably a biocompatible medical grade polymer such as, but not limited to, silicone, rubber, or a variety of thermoplastic elastomers (TPE) including polyvinyl chloride, polyethylene etc. Preferably, the menstrual cup is made of medical grade silicone or polysiloxane.

One or more parts of the menstrual cup 10 can optionally be made of a semi-rigid or rigid material. The walls of the storage receptacle 20, the barrier funnel 30, and the discharge duct 40 can have same or different thickness, elasticity and/or flexibility. The menstrual cup can be made transparent, translucent or opaque, with or without any coloration. In particular, the walls of the storage receptacle 20, the barrier funnel 30, and the discharge duct 40 can have same or different opacity, transparency or coloration.

The menstrual cup surface can be coated with one or more antimicrobial agents to prevent microbial growth and inhibit development of biofilm. The cup can also comprise microscale or nanoscale hierarchical topographical features on the surface to prevent microbial growth and adhesion to the surface, and/or to alter the wettability characteristics of the surface. The microscale or nanoscale hierarchical topographical features can be made by various techniques known in the art, such as imprinting, etching, soft lithography, solvent deposition, and/or embossing on the surface of the menstrual cup.

The cup can further comprise a blood repelling coating to provide a self-cleaning surface and prevent biofouling. In particular, the cup surface can be coated with superhydrophobic, ulrahydrophobic, and/or oleophobic coatings to mimic self-cleaning and antifouling properties found in nature, such as seen in surfaces demonstrating the Lotus effect. Additionally, blood repellency and superhydrophobicity can also be provided by modifying the surface topography of the cup surface on a micro or nano scale to reduce platelet adhesion and alter protein adsorption in a way that is not conducive to thrombus formation.

The present invention can also be used as a vaginal insert device for managing, alleviating, or eliminating other physical conditions and medical disorders such as female urinary incontinence, pelvic organ prolapse (POP), or both. This product provides additional advantages in that it does not require a prescription, is inexpensive, does not retain odor, and is easy for a user to insert and remove. Preferably such a vaginal insert device is reusable, but it can also be disposable. It eliminates the concern of toxic shock syndrome (TSS) by not comprising any absorbency element that could breed bacteria.

The invention is, of course, not limited to the embodiments described above, and equivalent variations or substitutions may be made by those skilled in the art without departing from the spirit of the invention, and such equivalents or alternatives are encompassed within the metes and bounds of the claims of the present application.

It should be further understood that the drawings are not necessarily to scale; instead, emphasis has been placed upon illustrating the principles of the invention. Moreover, the term "substantially" and "approximately" as used herein may be applied to modify any quantitative representation that could permissibly vary without resulting in a change in the basic function to which it is related.

It is also to be understood that the following claims are intended to cover all of the generic and specific features of the invention herein described and all statements of the scope of the invention which, as a matter of language, might be said to fall therebetween.

What is claimed is:

1. A menstrual cup configured for use in a vaginal canal to collect menstrual discharge, the menstrual cup comprising:

a storage receptacle, the storage receptacle having an internal surface defining a cavity for collecting and storing menstrual blood;

a barrier funnel, the barrier funnel having a folded position and an open position;

a discharge duct, the discharge duct having an upper end and a lower end;

a first flexible hinge, the first flexible hinge connecting the storage receptacle to the barrier funnel and allowing the barrier funnel to be moved relative to the storage receptacle between the folded position and the open position;

a second flexible hinge, the second flexible hinge connecting the barrier funnel to the discharge duct; and one or more inlet apertures disposed proximate the lower end of the discharge duct, the one or more inlet apertures configured to allow passage of menstrual discharge into the cavity of the storage receptacle;

wherein the menstrual cup is configured to be selectively changed between an elongated configuration and a compact configuration, wherein when the menstrual cup is in the elongated configuration, the first flexible hinge and the second flexible hinge are spaced apart from each other substantially along a longitudinal axis of the menstrual cup and the second hinge is disposed outside the cavity of the storage receptacle, and wherein when the menstrual cup is in the compact configuration, the first flexible hinge and the second flexible hinge are spaced apart from each other substantially along the longitudinal axis of the menstrual cup and the second hinge is disposed inside the cavity of the storage receptacle.

2. The menstrual cup of claim 1, wherein when the menstrual cup is in the elongated configuration, the barrier funnel and the discharge duct are disposed substantially outside the cavity of the storage receptacle, and wherein when the menstrual cup is in the compact configuration, the barrier funnel and the discharge duct are disposed substantially inside the cavity of the storage receptacle.

3. The menstrual cup of claim 1, wherein the second flexible hinge enables the discharge duct to be moved between a retracted position and an extended position.

4. The menstrual cup of claim 1, wherein the discharge duct comprises at least one discharge aperture at or substantially proximate the upper end of the discharge duct.

5. The menstrual cup of claim 1, wherein the upper end of the discharge duct is shaped substantially like a knob.

6. The menstrual cup of claim 5, wherein the discharge duct comprises at least one discharge aperture at or substantially proximate the upper end of the discharge duct.

7. The menstrual cup of claim 1, wherein the storage receptacle comprises a retrieving handle extending from a bottom portion of the storage receptacle, wherein the retrieving handle is configured to be gripped by user for removal of the menstrual cup from the vaginal canal.

8. The menstrual cup of claim 7, wherein the retrieving handle is shaped as an elongated stem.

9. The menstrual cup of claim 1, wherein when the menstrual cup is in the compact configuration, the second flexible hinge is disposed inside the cavity at substantially 10-90% depth of the cavity.

10. The menstrual cup of claim 9, wherein when the menstrual cup is in the compact configuration, the second flexible hinge is disposed inside the cavity at substantially 50% depth of the cavity.

11. The menstrual cup of claim 1, wherein the menstrual cup is made from a material comprising one or more of silicone, rubber, and thermoplastic elastomers.

12. The menstrual cup of claim 1, wherein the menstrual cup is made from medical grade silicone.

13. The menstrual cup of claim 1, wherein the first flexible hinge and the second flexible hinge are substantially coaxial.

14. The menstrual cup of claim 1, wherein the second flexible hinge has a diameter that is less than diameter of the first flexible hinge.

15. The menstrual cup of claim 14, wherein a ratio of the diameter of the second flexible hinge to the diameter of the first hinge is in a range of 0.10-0.90.

16. The menstrual cup of claim 1, wherein the menstrual cup is configured to be positioned in the vaginal canal in the compact configuration for collecting menstrual blood.

17. The menstrual cup of claim 1, wherein when the barrier funnel is in the folded position, an internal surface of the barrier funnel is configured to confine menstrual blood within the storage receptacle even when the menstrual cup is disposed in inclined or inverted orientations.

18. The menstrual cup of claim 1, wherein the menstrual cup is configured to drain collected menstrual blood out of the cavity under gravity when the menstrual cup is in the elongated configuration and disposed in an inverted position outside the vaginal canal.

\* \* \* \* \*